(12) United States Patent
Wolferseder

(10) Patent No.: US 9,939,395 B2
(45) Date of Patent: Apr. 10, 2018

(54) METHOD FOR MEASURING ASH/SLAG DEPOSITION IN A UTILITY BOILER

(75) Inventor: Thomas J. Wolferseder, Waterbury, CT (US)

(73) Assignee: Environmental Energy Services, Inc., Sandy Hook, CT (US)

( * ) Notice: Subject to any disclaimer, the term of this patent is extended or adjusted under 35 U.S.C. 154(b) by 1261 days.

(21) Appl. No.: 12/152,748

(22) Filed: May 16, 2008

(65) Prior Publication Data

US 2008/0291965 A1   Nov. 27, 2008

(51) Int. Cl.
| | |
|---|---|
| *G01N 25/08* | (2006.01) |
| *G01N 25/32* | (2006.01) |
| *G01N 25/72* | (2006.01) |
| *G01N 3/06* | (2006.01) |
| *G01N 3/56* | (2006.01) |
| *G01N 17/02* | (2006.01) |
| *G01N 25/18* | (2006.01) |

(52) U.S. Cl.
CPC ................... *G01N 25/18* (2013.01)

(58) Field of Classification Search
CPC ........ G01N 25/46; G01N 25/02; G01N 25/08; G01N 25/32; G01N 25/72; G01N 3/06; G01N 3/56; G01N 17/02
USPC .......... 374/4, 5, 57, 43, 44, 45, 100, 101, 2, 374/103, 179, 141, 7, 29, 301, 30, 1, 102, 374/137, 166, 167, 147, 148
See application file for complete search history.

(56) References Cited

U.S. PATENT DOCUMENTS

| | | | | |
|---|---|---|---|---|
| 2,237,036 A | * | 4/1941 | Krogh | G01K 1/125 136/233 |
| 2,758,793 A | * | 8/1956 | Stoops et al. | 236/20 R |
| 3,285,787 A | * | 11/1966 | Ehrler | G01K 1/14 136/231 |
| 3,519,254 A | * | 7/1970 | Putman | F23N 1/082 236/15 E |
| 3,530,716 A | * | 9/1970 | Schernthaner | C21C 5/4673 136/234 |
| 3,577,784 A | * | 5/1971 | Kovacic | C10B 45/00 201/1 |
| 3,918,300 A | * | 11/1975 | Weisstuch et al. | 73/113.01 |

(Continued)

FOREIGN PATENT DOCUMENTS

| | | | | |
|---|---|---|---|---|
| DE | 19650983 A1 | * | 6/1998 | G01K 1/125 |
| JP | 58155324 A | * | 9/1983 | |
| JP | 59183354 A | * | 10/1984 | |

OTHER PUBLICATIONS

International Search Report dated Aug. 8, 2008 from corresponding PCT/US2008/006270.

*Primary Examiner* — Gail Kaplan Verbitsky
(74) *Attorney, Agent, or Firm* — Richard P. Gilly; Offit Kurman, P.C.

(57) ABSTRACT

A method for measuring ash/slag deposition in an operating utility boiler. The method has the following steps: i) providing a probe for the boiler wherein the probe has at least one thermocouple therein or thereon for measuring temperature; ii) measuring the temperature at the thermocouple at a baseline time; iii) measuring the temperature at least one thermocouple at a pre-determined time later than the baseline time; and iv) comparing the temperature at the baseline time to the temperature at the pre-determined time to correlate to a level of deposition. There is also a utility boiler system.

15 Claims, 11 Drawing Sheets

(56) References Cited

U.S. PATENT DOCUMENTS

| | | | | |
|---|---|---|---|---|
| 3,934,646 A * | 1/1976 | Robertson | G01N 17/00 | 165/104.21 |
| 3,974,691 A * | 8/1976 | Repetto | G01K 13/02 | 374/35 |
| 4,138,878 A * | 2/1979 | Holmes et al. | | 374/7 |
| 4,176,554 A * | 12/1979 | Kazmierowicz | | 374/137 |
| 4,195,596 A * | 4/1980 | Scheifley | B01D 53/70 | 122/149 |
| 4,383,438 A * | 5/1983 | Eaton | | 73/61.62 |
| 4,403,516 A * | 9/1983 | Mailliet | C21B 7/24 | 374/135 |
| 4,480,930 A * | 11/1984 | DeZubay et al. | | 374/134 |
| 4,488,516 A * | 12/1984 | Bueters et al. | | 122/379 |
| 4,488,866 A * | 12/1984 | Schirmer et al. | | 431/4 |
| 4,495,874 A * | 1/1985 | Greskovich et al. | | 110/347 |
| 4,516,510 A * | 5/1985 | Basic, Sr. | | 110/346 |
| 4,571,094 A * | 2/1986 | Wynnyckyj et al. | | 374/29 |
| 4,596,198 A | 6/1986 | Greskovich | | |
| 4,615,302 A * | 10/1986 | Wynnyckyj et al. | | 122/379 |
| 4,652,420 A * | 3/1987 | Smith | | 376/256 |
| 4,719,092 A * | 1/1988 | Bowers | | 423/235 |
| 4,722,610 A * | 2/1988 | Levert et al. | | 374/43 |
| 4,747,700 A * | 5/1988 | Lenz et al. | | 374/135 |
| 4,762,425 A * | 8/1988 | Shakkottai | G01K 11/24 | 367/902 |
| 4,854,729 A * | 8/1989 | Lovato | G01K 1/143 | 136/230 |
| 4,901,061 A * | 2/1990 | Twerdochlib | G01K 3/14 | 340/501 |
| 5,050,108 A * | 9/1991 | Clark et al. | | 702/34 |
| 5,108,192 A * | 4/1992 | Mailliet | C21C 5/4673 | 136/230 |
| 5,226,730 A * | 7/1993 | Berthold | G01K 11/24 | 374/117 |
| 5,271,674 A * | 12/1993 | Kalmanovitch | | 374/16 |
| 5,275,553 A * | 1/1994 | Frish et al. | | 431/76 |
| 5,353,653 A * | 10/1994 | Watanabe et al. | | 73/865.9 |
| 5,399,017 A * | 3/1995 | Droege | | 374/7 |
| 5,431,495 A * | 7/1995 | Hemsath | G01N 25/08 | 266/100 |
| 5,454,977 A * | 10/1995 | Shimizu et al. | | 252/299.61 |
| 5,563,803 A * | 10/1996 | Morihara et al. | | 700/274 |
| 5,615,953 A * | 4/1997 | Moskal | | 374/7 |
| 5,740,745 A * | 4/1998 | Smyrniotis et al. | | 110/343 |
| 5,863,123 A * | 1/1999 | Lee | G01K 7/04 | 136/230 |
| 6,048,510 A * | 4/2000 | Zauderer | | 423/235 |
| 6,288,528 B1 * | 9/2001 | Goodstine et al. | | 324/71.1 |
| 6,375,346 B1 * | 4/2002 | Lunsford | | 374/4 |
| 6,485,174 B1 * | 11/2002 | Albrecht | G01K 17/08 | 374/147 |
| 6,568,846 B1 * | 5/2003 | Cote et al. | | 374/5 |
| 6,644,848 B1 * | 11/2003 | Clayton et al. | | 374/7 |
| 6,978,663 B1 * | 12/2005 | Sinquefield | G01N 17/008 | 436/6 |
| 7,077,563 B2 * | 7/2006 | Xiao et al. | | 374/29 |
| 7,469,077 B2 * | 12/2008 | Xia | G01K 11/3206 | 374/E11.016 |
| 7,607,825 B2 * | 10/2009 | Koschack | F23J 3/02 | 374/121 |
| 8,147,130 B2 * | 4/2012 | Sakami | G01B 21/085 | 374/134 |
| 2004/0086020 A1 * | 5/2004 | Jordahl | | 374/45 |
| 2006/0032606 A1 * | 2/2006 | Thybo et al. | | 165/11.1 |
| 2006/0257799 A1 * | 11/2006 | Nowak et al. | | 431/4 |
| 2008/0201980 A1 * | 8/2008 | Bullinger et al. | | 34/493 |
| 2008/0298426 A1 * | 12/2008 | Koschack et al. | | 374/7 |
| 2009/0262777 A1 * | 10/2009 | Sakami | G01B 21/085 | 374/7 |
| 2011/0144790 A1 * | 6/2011 | Gerritsen | G01K 1/026 | 700/108 |

* cited by examiner

METHOD FOR MEASURING ASH/SLAG DEPOSITION IN A UTILITY BOILER

CROSS-REFERENCE TO A RELATED APPLICATION

The present application claims priority based on U.S. Provisional Application No. 60/930,804, filed May 18, 2007, which is incorporated herein by reference in its entirety.

BACKGROUND OF THE INVENTION

1. Field of the Invention

The present invention relates to a method of the present invention for measuring ash/slag deposition in an operating utility boiler.

2. Description of the Related Art

Utility boilers or furnaces are employed in industry for generation of heat, production of steam, and generation of electricity utilizing steam. Utility boilers typically have a furnace therein wherein a fossil fuel, such as residual oil, #6 fuel oil or coal, is oxidized or burned to generate heat. Along with generating heat, utility boilers will generate or evolve an exhaust gas that will contain carbon dioxide (product of oxidation of fuel oil), residual oxygen (unreacted), inert air components, i.e., nitrogen and argon, and emissions, such as sulfur-based and nitrogen-based compounds. Exhaust gas is typically treated and then vented to the atmosphere.

A problem with the operation of a boiler or furnace is the buildup of ash and/or slag deposits on internal boiler and heat exchanger contact surfaces. The buildup impedes heat transfer and can cause boiler or furnace temperatures to rise unnecessarily and/or diminish steam production and/or otherwise diminish efficient operation of the boiler or furnace.

Buildup of ash and/or slag has proven difficult to characterize and measure over the course of operation of the boiler or furnace.

Effective characterization and measure of buildup would enable operating conditions within the boilers and furnaces to be optimized or regulated to best advantage.

It would be desirable to have a method for measuring the buildup of slag and/or ash deposition in boilers or furnaces. It would be further desirable to be able to carry out such measurements in real-time method.

SUMMARY OF THE INVENTION

According to the present invention, there is provided a method for measuring ash/slag deposition in an operating utility boiler. The method has the following steps: i) providing a probe for the boiler wherein the probe has at least one thermocouple therein or thereon for measuring temperature; ii) measuring the temperature at the thermocouple at a baseline time; iii) measuring the temperature at least one thermocouple at a pre-determined time later than the baseline time; and iv) comparing the temperature at the baseline time to the temperature at the pre-determined time to correlate to a level of deposition.

According to the present invention, there is provided a utility boiler system. The system has a boiler and a removable probe having at least one thermocouple therein or thereon for measuring temperature.

DETAILED DESCRIPTION OF THE INVENTION

The use of the method of the invention permits real-time review of the level and/or rate of ash/slag deposition occurring for given process conditions. The real-time review permits the deposition process to be monitored more closely and, thus, minimized.

The longer a boiler/furnace operates, the more ash or slag that deposits on internal boiler and heat exchanger contact surfaces. As deposition increases, the temperature indicated by a thermocouple will decrease. The level of temperature decrease correlates inversely to increase in deposition.

Figure 1:
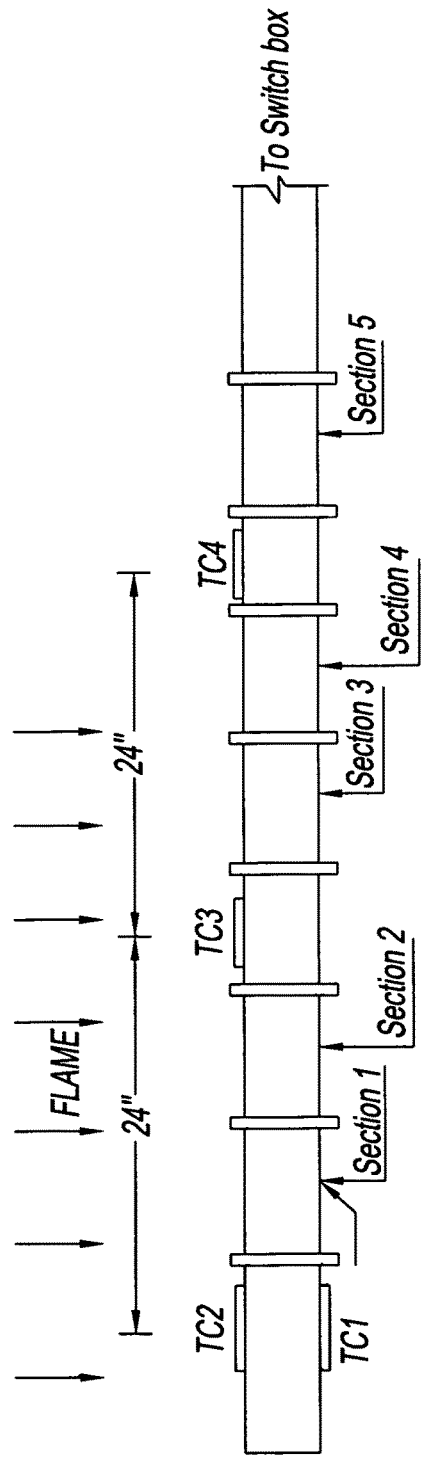
FIG. 1 shows a representational view of an example of a high temperature probe useful in carrying out the method of the present invention.
Figure 2:
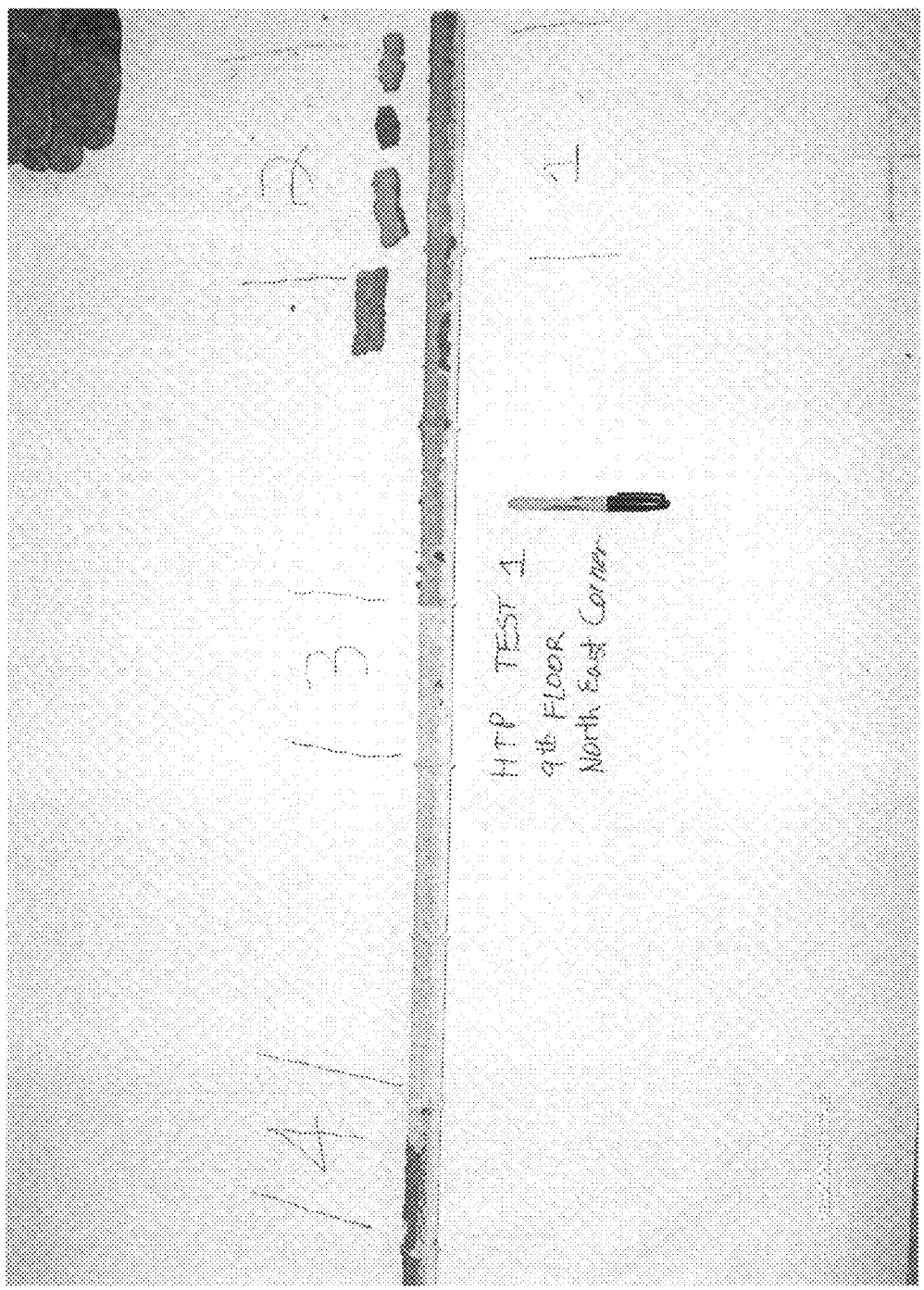
FIG. 2 shows an image of a photographic high temperature probe employed in HTP Test 1.
Figure 3:
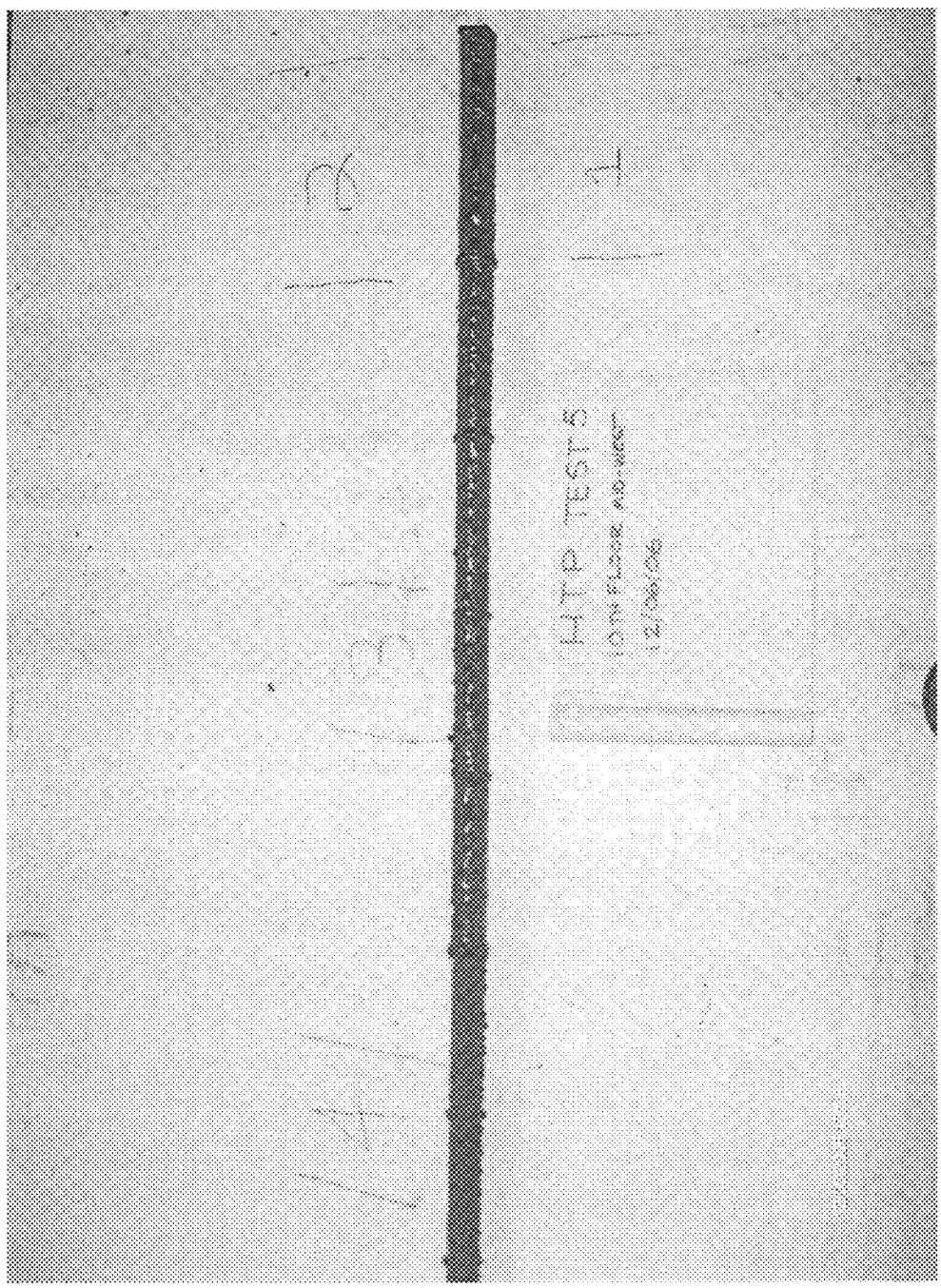
FIG. 3 shows a photographic image of a high temperature probe employed in HTP Test 5.
Figure 4:
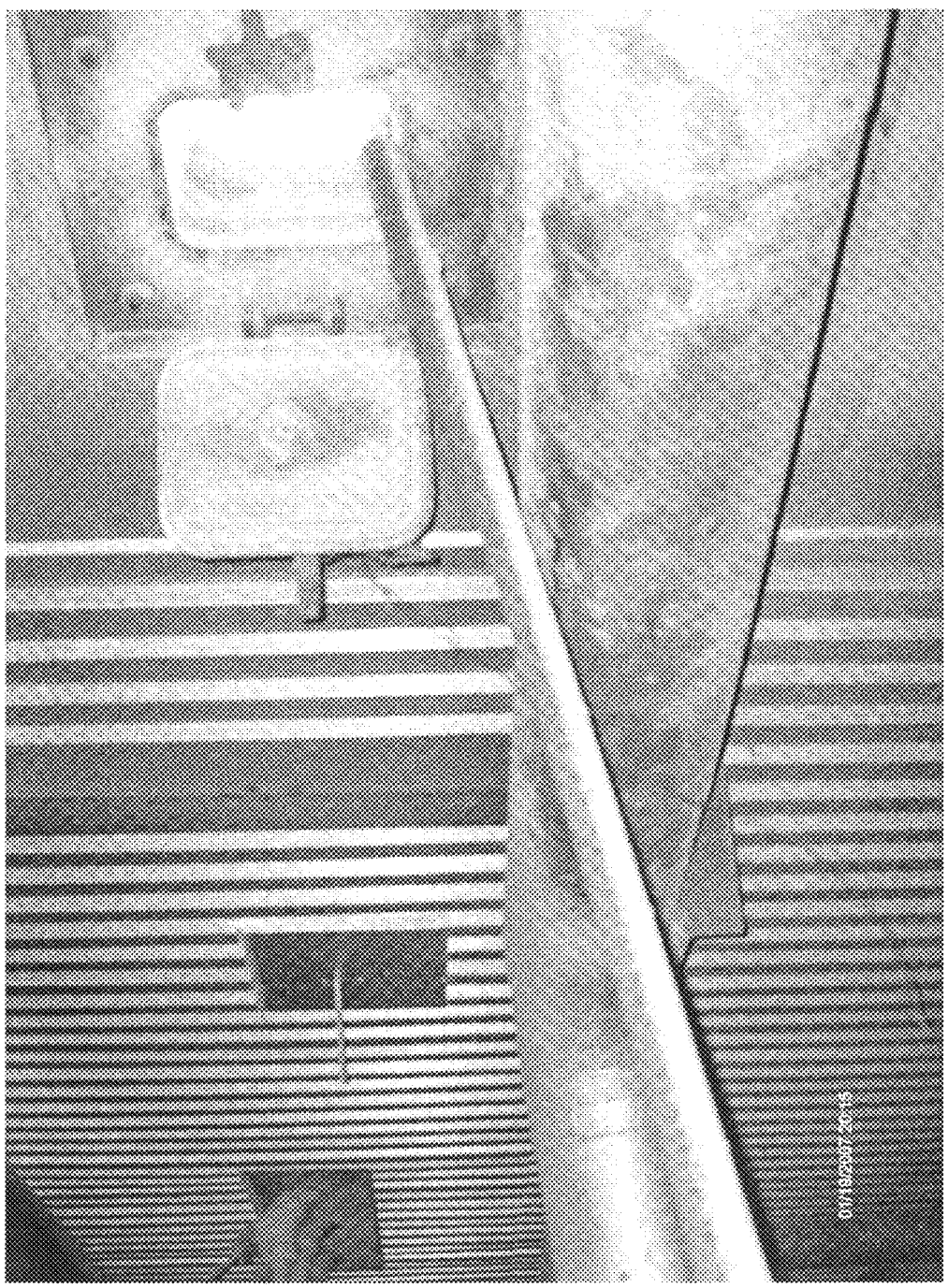
FIG. 4 shows a photographic image of a high temperature probe being removed from a boiler.
Figure 5:
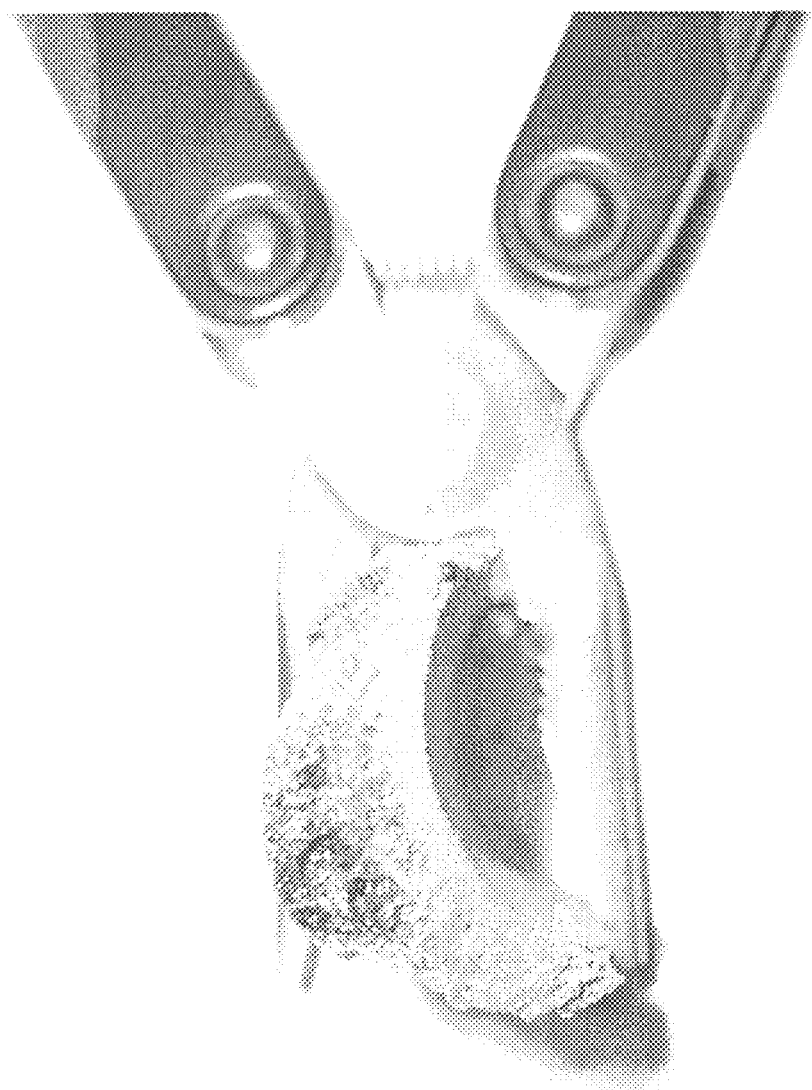
FIG. 5 shows a photographic image of a section of an ash deposit removed from a high temperature probe.
Figure 6:
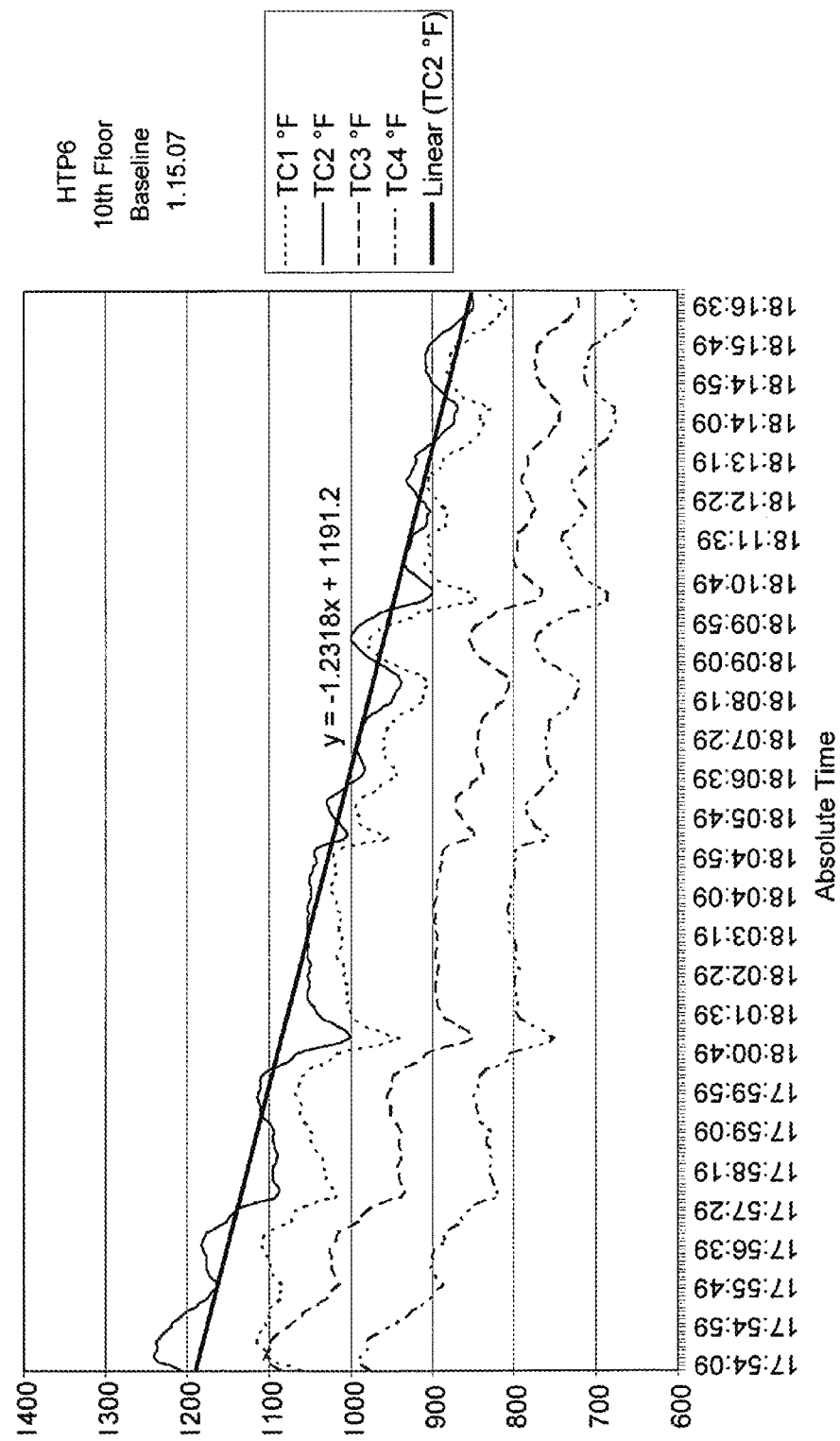
FIG. 6 shows a plot of temperature profiles for HTP6 $10^{th}$ Baseline Jan. 15, 2007.
Figure 7:
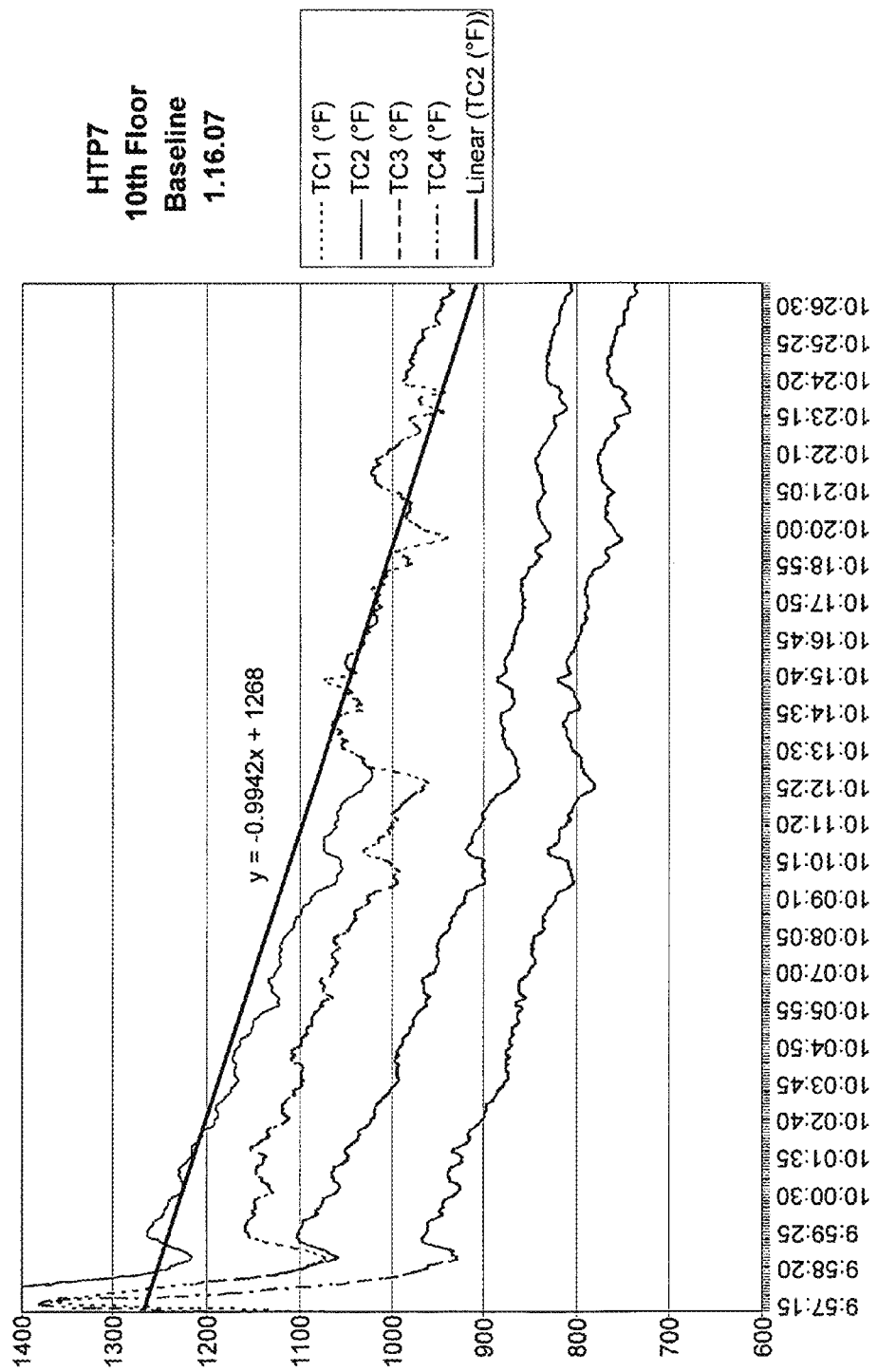
FIG. 7 shows a plot of temperature profiles for HTP7 $10^{th}$ Baseline Jan. 16, 2007.
Figure 8:
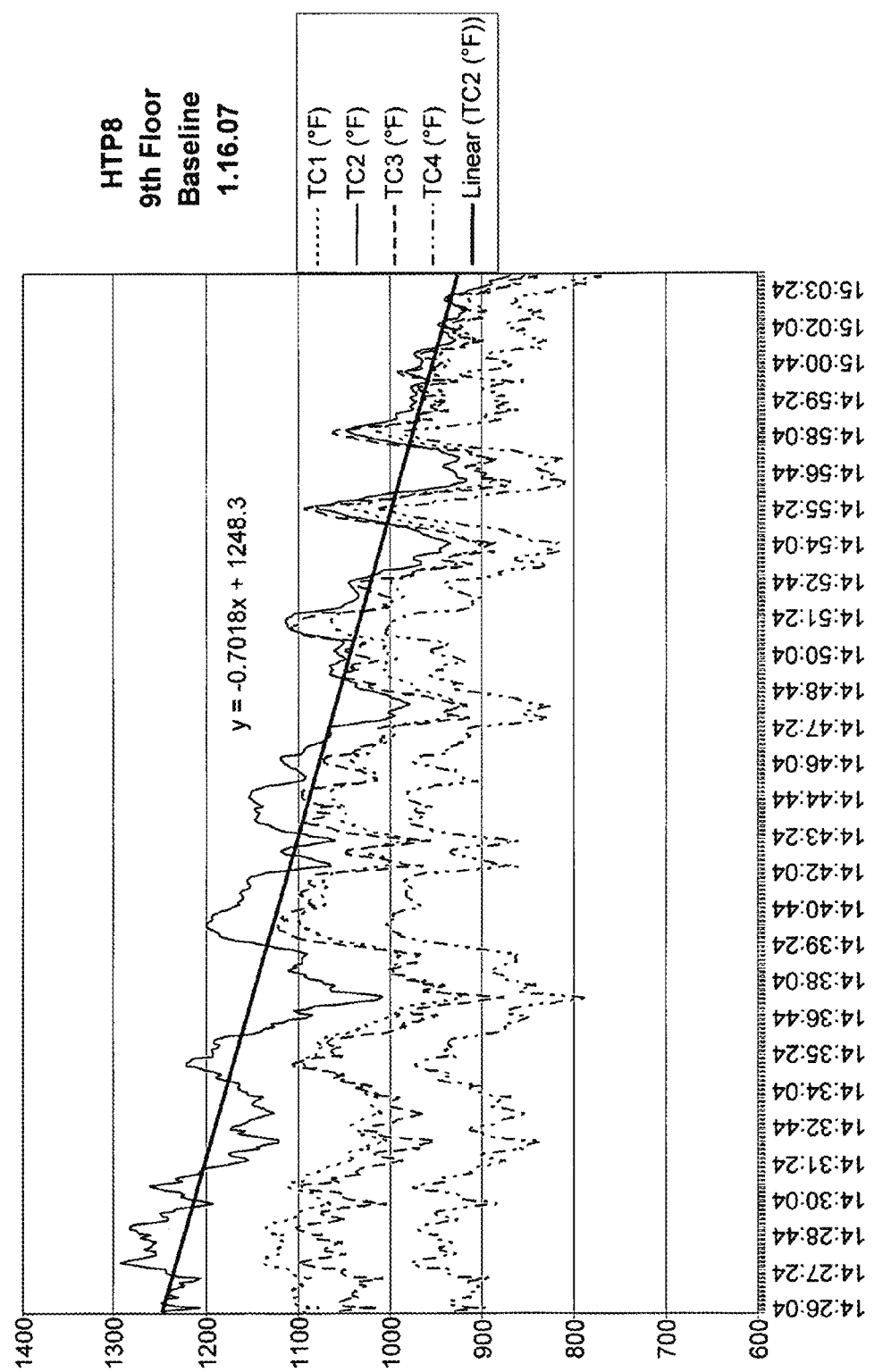
FIG. 8 shows a plot of temperature profiles for HTP8 $9^{th}$ Baseline Jan. 16, 2007.
Figure 9:
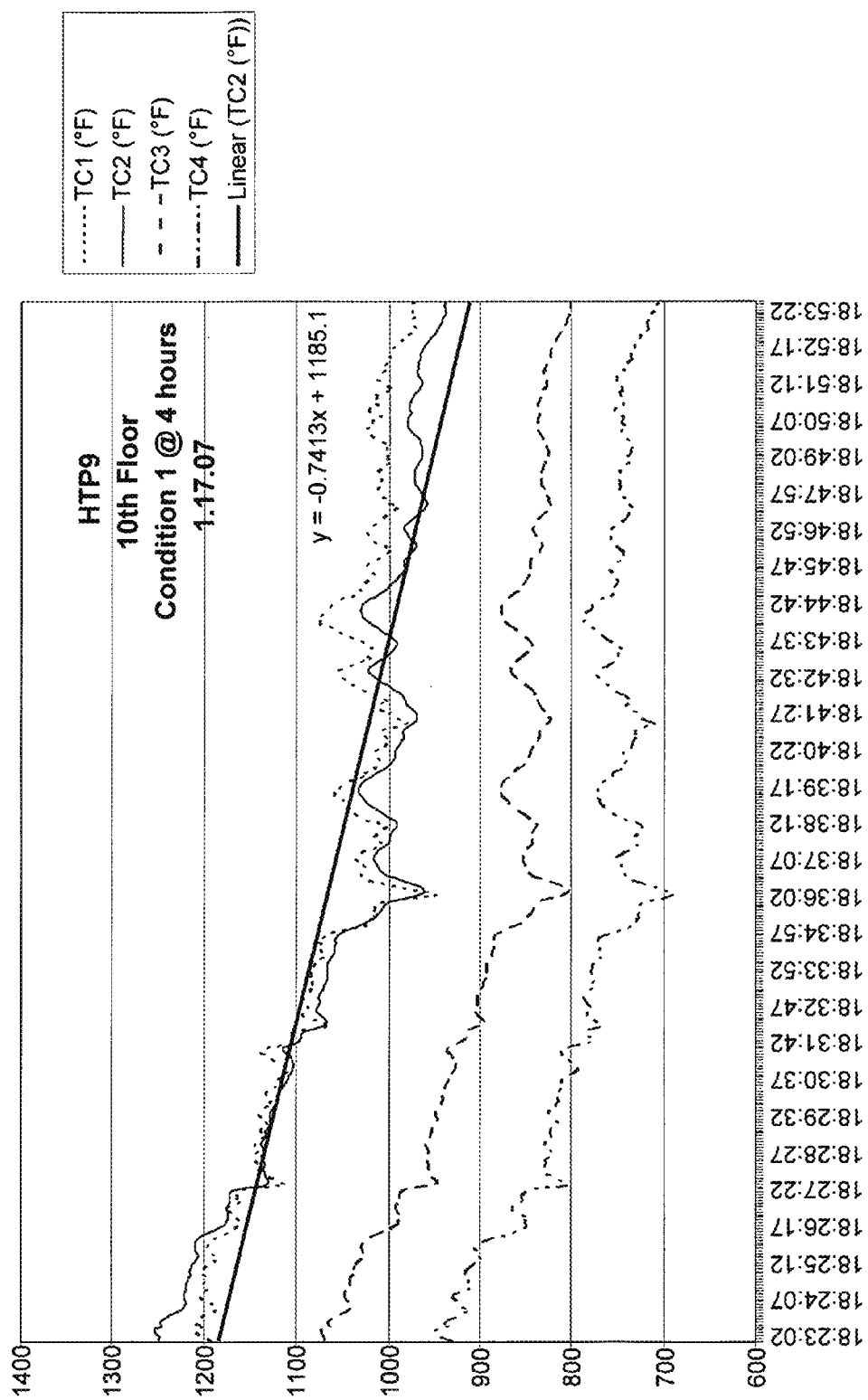
FIG. 9 shows a plot of temperature profiles for HTP9 $10^{th}$ Condition 1 @ 4 hours Jan. 15, 2007.
Figure 10:
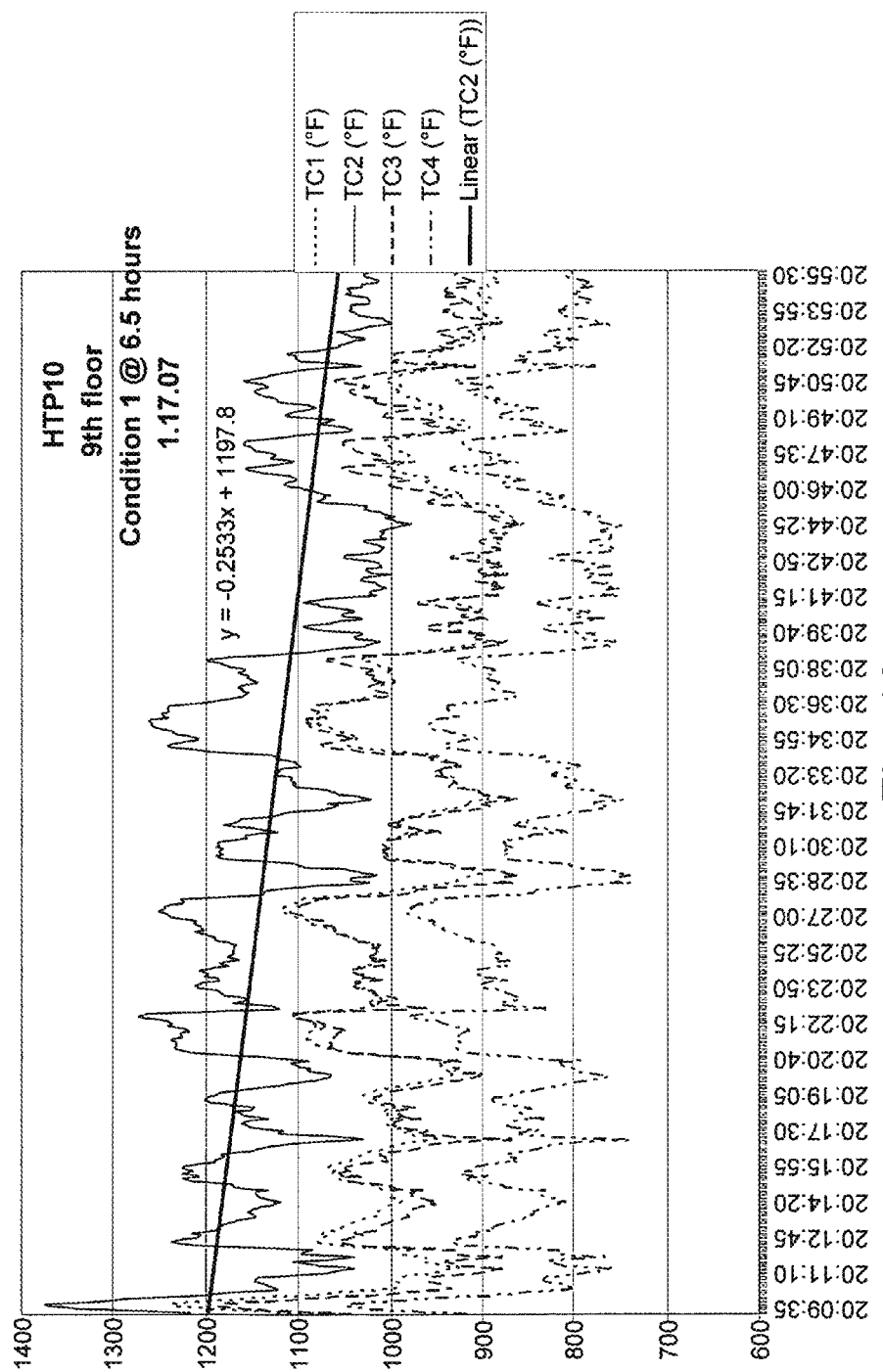
FIG. 10 shows a plot of temperature profiles for HTP10 $10^{th}$ Condition 1 @ 6.5 hours Jan. 17, 2007.
Figure 11:
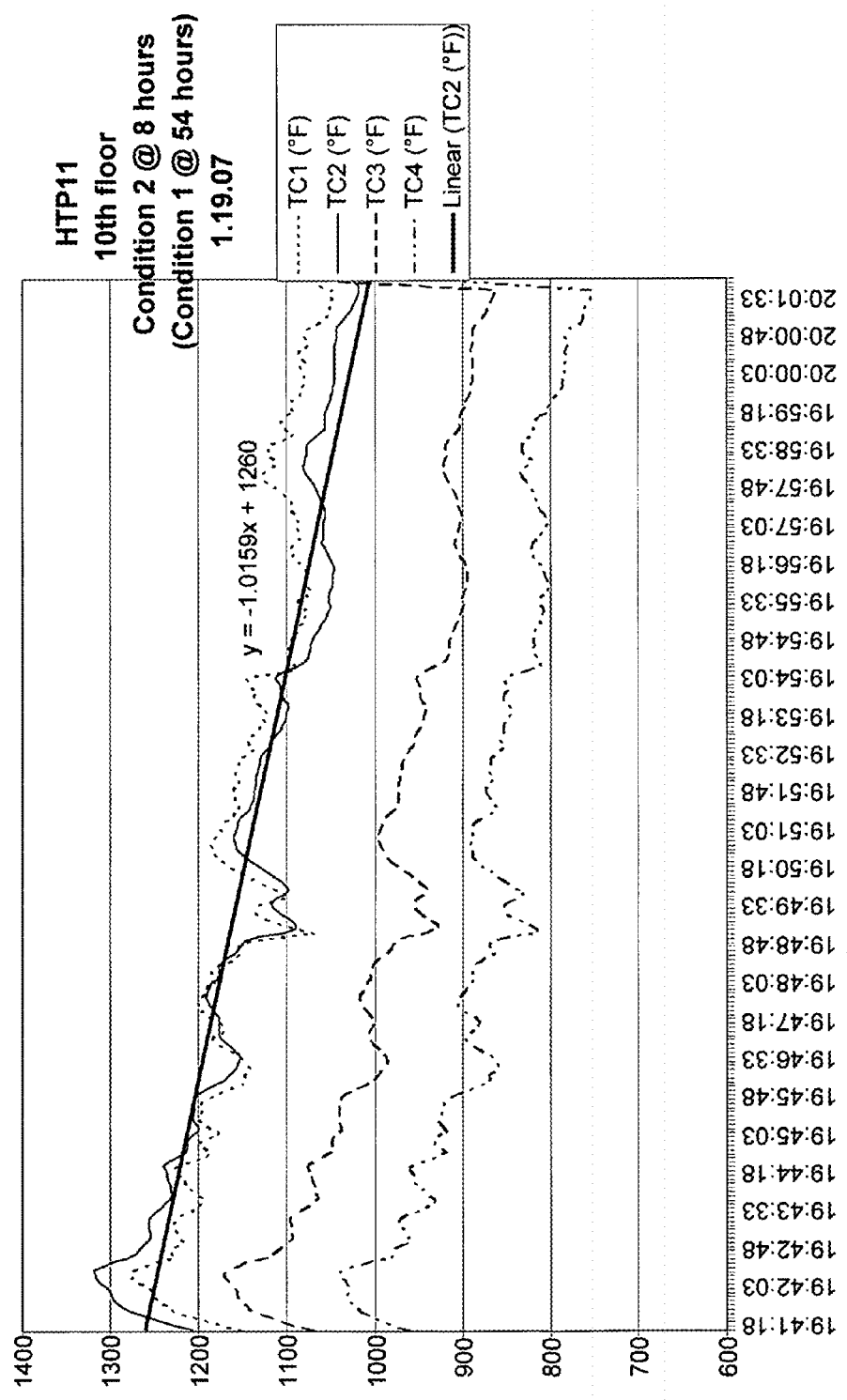
FIG. 11 shows a plot of temperature profiles for HTP11 $10^{th}$ Condition 2 @ 8 hours (Condition 1 @ 4 hours) Jan. 19, 2007.

The HTP or slag probe useful in the present invention is constructed of a high-temperature alloy and is insertable and removable/retractable from the boiler/furnace. The probe has at least one and preferably a plurality of thermocouples to measure temperature. The probe preferably takes the general shape of a rod, pole, or lance with thermocouples positioned at points therealong. Thermocouples may also be positioned to be oriented toward or away from (or both) the flame within the boiler/furnace. The probe is preferably air-cooled to maintain particular temperature conditions within the probe. The temperature of the probe is maintained independently of the temperature within the boiler/furnace. An example of a useful probe is shown in the FIG. 1.

Although not critical to the present invention, deposition or buildup can be controlled in boilers and furnaces by a variety of methods Those methods include (i) use of slag control agents and oxygen-generating agents; (ii) control of process variables such as temperature, pressure, and air feed rate; and (iii) control of feedstock composition.

A slag control agent is optionally employed to prevent buildup of deposits within the furnace of the utility boiler and other process surfaces. The slag control agent reacts with sulfuric acid to form innocuous, non-acidic compounds, thereby reducing acid emissions and corrosion of process surfaces within the utility boiler. The slag control agent also reacts or complexes with any undesirable vanadium compounds that may be present in the fuel oil. Conversion of undesirable vanadium compounds, such as vanadium pentoxide and sodium vanadium pentoxide, to more innocuous vanadium compounds or forms helps to prevent or reduce catalysis of sulfur dioxide to sulfur trioxide, corrosion of process surfaces due to acid exposure, and deposition of vanadium compounds on process surfaces inside the utility boiler. Slag control agents are useful in both oil-fired and coal-fired boilers.

Useful slag control agents include, but are not limited to, the following: magnesium hydroxide; magnesium oxide; magnesium carbonate; and magnesium organometallic compounds, such as magnesium carboxylate, magnesium salicylate, magnesium naphthenate, and magnesium sulfonate. Preferred slag control agents are magnesium hydroxide, magnesium oxide, and organometallic magnesium carboxylate with magnesium carbonate overlay.

An oxygen-generating agent is optionally employed to provide additional oxygen at the situs of oxidation or burning in the furnace, which allows the feed rate of air supplied to the utility boiler to be reduced and/or minimized. Use of the oxygen-generating agent also reduces the incidence of unburned carbon due to more efficient combustion or burning. Reduction of unburned carbon also reduces the incidence and retention of sulfuric acid, which is absorbed by unburned carbon. Oxygen-generating agents are useful in both oil-fired and coal-fired boilers.

Useful oxygen-generating agents include, but are not limited to, the following: calcium nitrate, calcium organometallic compounds, calcium salicylate, calcium sulfonate, overbased calcium carboxylate, iron oxides, iron carboxylates, iron organometallic compounds, iron sulfonates, barium oxide, barium carbonate, barium carboxylate, barium organometallic compounds, and barium sulfonate. Preferred oxygen-generating agents are the calcium compounds. Most preferred oxygen-generating agents are calcium nitrate and calcium carboxylate.

The slag control agent and the oxygen-generating agent can be added or mixed into the fuel oil prior to combustion or added into the furnace of the utility boiler during combustion or burning. The treatment of the fuel oil can be homogeneous or non-homogeneous, i.e., the agents can be homogeneously admixed within the fuel oil or non-homogeneously applied, such as to the surface or some portion of the fuel oil. The slag control agent and the oxygen-generating agent can be added or mixed in like manner in coal-fired boilers.

The slag control agent and the oxygen-generating agent can be used in any known product form, such as a powder or liquid. Liquids may be water-based, oil-based, or a combination thereof. Liquids may take any known liquid form, such as solutions, slurries, suspensions, dispersions, or emulsions. Liquid forms are preferred since they can be injected or sprayed with precision via conventional pumping and metering devices. A preferred means of adding the slag control agent and the oxygen-generating agent to the fuel oil or coal is via injection in liquid form.

The amount of slag control agent employed will vary depending upon a variety of process and composition conditions, such as type of slag control agent selected, load or feed rate of fuel oil or coal, amount and type of oxygen-generating agent used, percent of excess oxygen desired, amount or feed rate of air, impurity composition of fuel oil or coal, and the like. When a liquid form of the slag control agent is used, the amount employed will typically vary from about 1:2000 to about 1:6000 agent:fuel oil, volume:volume.

The amount of oxygen-generating agent employed will vary depending upon a variety of process and composition conditions, such as type of oxygen-generating agent selected, load or feed rate of fuel oil, amount and type of slag control agent used, percent of excess oxygen desired, amount or feed rate of air, impurity composition of fuel oil, and the like. When a liquid form of the oxygen-generating agent is used, the amount employed will typically vary from about 1:1000 to about 1:10000 and preferably about 1:2500 to about 1:4000 agent:fuel oil, volume:volume.

An advantage of the present invention is characterization and control/minimization of slag deposition on process surfaces within the boiler/furnace and other process surfaces in contact with the exhaust gas. Slag deposition can take the form of one or more layers caked/baked onto process surfaces. For instance, slag can deposit on the surfaces of tube bundles or other heat transfer devices within the utility boiler denuding the heat transfer efficiency of the utility boiler. An inner layer typically takes the form of metal complexes of vanadium with sodium, nickel, or iron. The vanadium/sodium, vanadium/nickel, and vanadium/iron metal complexes exhibit relatively low melting points, i.e., 1000° F. to 1700° F. and leave a sticky deposit or buildup on process surfaces. Another layer may form on the inner layer and take the form of vanadium/magnesium complexes exhibiting slightly higher melting points than the vanadium/sodium, vanadium/nickel, or vanadium/iron complexes. The vanadium/magnesium metal complexes are water soluble and friable, and can be washed and easily removed by conventional techniques, such as soot blowing. However, if elevated amounts of slag control agent, such as magnesium oxide, are used, the slag control agent may deposit on the surfaces of the layers of the metal complexes and be difficult or impossible to remove. Magnesium oxide, a commonly used slag control agent, for example, is not water soluble or friable and is very difficult to remove by conventional techniques.

Another advantage of the present invention is characterization and control/minimization of ash deposition on process surfaces within the boiler/furnace and other process surfaces in contact with the exhaust gas. Ash deposition occurs in both oil-fired and coal-fired boilers, but is a particular problem in coal-fired boilers due to the considerable ash content in coal. Ash takes the form of noncombustible metals and/or minerals. The physical properties of ash vary depending on its composition depending on the properties of the ash. Ash may take a liquid or a solid deposition form in an operating boiler depending on the properties of the ash. Ash deposition on tube surfaces and other process surfaces impedes heat transfer and can cause boiler temperatures to rise unnecessarily and/or diminish steam production and/or otherwise diminish efficient operation of the boiler.

Additional teachings regarding the operation of utility boilers and furnaces are shown in U.S. Patent Publication No. 2006/0257799 A1, which is incorporated herein by reference.

The following are non-limiting examples of the method of the claimed invention.

EXAMPLES

In the following examples, time versus temperature can be measured and set forth in plots/graphs. For one means of analysis, a linear regression line is drawn through the data points to yield a slope. A lower slope indicates slower deposition (slower buildup) and a higher slope indicates faster deposition (faster buildup). The use of the method of the invention permits real-time review of the level and/or rate of ash/slag deposition occurring for given process conditions. The real-time review permits the deposition process to be monitored more closely and, thus, minimized.

The HTP, or "slag probe", is a temperature controlled thermocoupled high alloy furnace probe that duplicates generating tube surface metal temperatures to establish baseline data vs. treatment with fuel additives, characterize high temperature deposit formation and treatment modification. This diagnostic tool enables EES to establish product feed rate(s) based on fuel quality and furnace temperatures as well as to quantify the effectiveness of treatment. The slag probe will be used to determine deposit composition and provide samples for the ash porosity test.

HTP Probes were run on the $10^{th}$ floor pendant superheat section (center of the west side), and on the $9^{th}$ floor division superheat section (North East corner). The data is broken down by test number, location, zone 1 or 4, and condition (baseline, condition 1, and condition 2). The average HTP temperatures increase from Zone 4 to Zone 1 and represent the steam tube surface and subsequent insulating layers. Zone 1 and zone 4 were chosen for analysis to show hot region deposits (Z1) and cold region deposits (Z4). However, due to lack of buildup on the $9^{th}$ floor HTP's, only zone 1 was analyzed. All deposits were sent out for mineral analysis; 8 point fusion temperature analyses were performed only on the hot region deposits.

HTP results are summarized in the table on the following pages.

After condition 1 was reached with the CT300 treatment ($Mg(OH)_2$—magnesium hydroxide), the probe deposits showed visual modification as evidenced by the photos in Appendix iii. As treatment was continued, deposits would not stick to the probe, instead would bend up and pull away from the probe surface—see photo HTP 9. This indicates that the CT300 is interacting within the first eutectic melt phase and inhibiting the ash/slag buildup from bonding to the simulated tube surface.

After condition 2 was reached with Co-Treatment of CT300 and CT100 ($CuNH_3Ac$), the probe deposits were found to be visually different than HTP 9, see Trial Log and Notes above for HTP 11. The mineral analysis of the deposits confirms that a major change in composition has occurred by introducing CT100. More magnesium is brought into the deposit in both Zone 1 and Zone 4 along with a 50% drop in iron content. In the case of Zone 1 an increase in Copper of 85% was determined by ICP spectroscopy. A large shift in calcium and silica was also observed as evidenced by the lack of black glass on the condition 2 probe.

Analysis of the deposition rate data clearly shows a reduction in deposition of 35% for HTP 9 versus baseline. This does not as change much for Condition 2 but still represents a decrease with respect to baseline. The HTP temperature graphs in Appendix iv demonstrate how slag builds and sheds during Conditions 1 and 2 where as baseline probes yield graphs with consistent steeper slopes.

TABLE 1

(HTP Results Summary)

| HTP Location, Zone, Condition | MgO | CaO | $Fe_2O_3$ | $SiO_2$ | Cu | B/A Ratio | Red. Fusion Temp, FT. | Oxid. Fusion Temp., FT. |
|---|---|---|---|---|---|---|---|---|
| $9^{th}$ Floor HTP, Composite | ↑ 39% | ↑ 23% | ↓ 12% | ↓ 15% | N/A | ↑ 0.13 | N/A | N/A |
| $10^{th}$ Floor, Zone 1 (Hot Region), Condition 1 | ↑ 12% | ↑ 12% | ↓ 40% | ↓ 1% | N/A | ↓ 0.01% | ↑ 116° F. | ↑ 86° F. |
| $10^{th}$ Floor, Zone 1 (Hot Region), Condition 2 | ↑ 17% | ↑ 27% | ↓ 31% | ↓ 11% | ↓ 85% | ↑ 0.06 | ↑ 89° F. | ↑ 72° F. |
| $10^{th}$ Floor, Zone 4 (Cold Region), Condition 1 | ↑ 6% | ↓ 3% | ↓ 51% | ↑ 4% | N/A | ↓ 0.09% | ↑ 116° F. | ↑ 116° F. |
| $10^{th}$ Floor, Zone 4 (Cold Region), Condition 2 | ↑ 13% | ↑ 8% | ↓ 54% | ↑ 1% | N/A | ↓ 0.04% | ↑ 116° F. | ↑ 116° F. |

TABLE 2

(Notes and Observations)

| Date | Condition | Description | Notes |
|---|---|---|---|
| | | | Start at 5:55pm |
| | | | 18:18 probe shook; possible sootblower interference, make note in chart data |
| 15-Jan | Baseline | HTP 6, 10th floor | Caliper measurement of deposit thickness 0.15 inch Zone 1, 0.1 inch Zone 2; 0.12 inch Zone 3 |
| | | | Deposit is a brownish green rough ash with two layers - brown on the tube surface and dark brownish green on the surface. The surface has grey silver beads like black glass dripping. Overall a friable ash. |
| 15-Jan | Baseline | Slag Cup 10th Floor | Difficult removal - consistency of tar, strong adhesion to tube surface, hardens upon removal and cooling at ambient temp (130 F.) |

TABLE 2-continued (Notes and Observations)

| Date | Condition | Description | Notes |
|---|---|---|---|
| | | | Start at 5:55pm<br>18:18 probe shook; possible sootblower interference, make note in chart data |
| 16-Jan | Baseline | HTP 7, 10th floor | One hour test - Start Time 9:59:30 - Unit running at approx. 627 MWg - 10:12 SB sounds close to probe - probe hit at 10:13. Probe hit again at 10:22, Shed at approx 30 min. - 30 min HTP for baseline is standard at this location.<br>T/C2 0.5 inch Zone 1 0.2 inch Zone 2 0.2 inch T/C 3 0.2 inch Zone 4 0.2 inch T/C 4 0.2 inch Zone 5 0.23 inchTube surfaces relatively clean, friable deposits only - no glass like formations. Powder retrieved from tubes - not retained due to minimal amount |
| 16-Jan | Baseline | Slag Cup 9th Floor | Tube surfaces relatively clean, friable deposits only - no glass like formations. Powder retrieved from tube not retained due to minimal amount. |
| 16-Jan | Baseline | Slag Cup 6½ Floor | Tube surfaces 30-40% glass-like deposits on wall, Sample not taken due to spotty wall coverage One Hour Test - Start Time approx 2:25 pm North East Corner, minimal buildup on walls - sulfate like coating (white-pink-white) where covered.<br>Visually, about ½ inch of dripping glass-like slag began forming on tip of probe, then shed due to probe. |
| 16-Jan | Baseline | Slag Cup 8, $9^{TH}$ Floor | movement/flexing: Much less buildup on probe than 10th floor; indicating that there is less of a fluxing agent (Ca or Na) in this region. Friable popcorn like deposit over hot regions of probe, light tan tenacious dusting on entire probe as first layer<br>T/C2 = 0.15 inch; Zone 1 = <.062 inch; Remainder of probe not sampled due to insufficient accumulation To be sent out for analysis |
| 16-Jan | Baseline | Coal Sample | We took 6 videos across the North Wall on the 10th floor. Pendants have heavy slag buildup as does the East Water Wall 2 |
| 16-Jan | Baseline | IR Camera | Deposit lifted off the probe indicating lack of glue on the tube surface. The deposit was friable with no black glass. |
| 17-Jan | Condition 1 | Slag Cup 9, $10^{TH}$ Floor | Deposit is more narrow but still thick. Brown layer about ½ inch from tube surface with a thin greyish layer on top. A few black/grey beads.<br>T/C2 = 0.4 inch; Zone 1 = 0.3 inch; Zone 2 = 0.3 inch; T/C 3 = 0.3 inch 7:35PM The slag is brittle, no tar like substance (black glass). 3 foot piece knocked off the tube |
| 17-Jan | Condition 1 | Slag Cup 9, $10^{TH}$ Floor | while probing for a sample. |
| 17-Jan | | Slag Cup 9, $10^{TH}$ Floor | Distinct difference in gas flow pattern on probe. Probe was bending down instead of up. Deposit buildup is |
| 19-Jan | Condition 2 | Slag Cup 11, 10th Floor | very porous and brownish green with grey pearls scattered about in color. No discernable layering. Deposit is also peeling up from the probe Slag is easily removed and looks the same as our probe deposit. Very porous with some black glass |

TABLE 2-continued (Notes and Observations)

| Date | Condition | Description | Notes |
|---|---|---|---|
| | | | Start at 5:55pm |
| | | | 18:18 probe shook; possible sootblower interference, make note in chart data |
| 19-Jan | Condition 2 | Slag Cup 10th Floor | pearls on the surface. As compared to condition 1: Sample is much less dense and lighter in color. Crystal structure is much more porous and friable on Cond. 2. 50% as thick as Cond. 1 |
| 23-Jan | Condition 4 | Slag Cup 12, 10th Floor | Slag was very friable and broke off the probe during removal from the boiler. Test was repeated to get samples for analysis. |
| 23-Jan | Condition 4 Repeat | Slag Cup 12, 10th Floor | CT-100 running at 12 gph (30/70 blend with CT-. 300). Deposits were very friable |
| 25-Jan | | No Testing | Return to CT-300 only to run out the tanks. Plant performed a thermal shock tonight. |

HTP data is set forth in the following paragraphs.

HTP 6:
Jan. 15, 2007 17:54-18:17
$10^{th}$ Floor—Baseline—60 min. reduced to 23 min.
$T_2$ Slope: −1.2318
$T_2$ Start Temp: 1191
$T_2$ End Temp: 850
Difference: −341 (−14.8 deg/min)

HTP 7:
Jan. 16, 2007 9:57-10:27
$10^{th}$ Floor—Baseline—60 min. reduced to 30 min.
$T_2$ Slope: −0.9942
$T_2$ Start Temp: 1268
$T_2$ End Temp: 943
Difference: −325 (−10.8 deg/min.)

HTP 8:
Jan. 16, 2007 14:26-15:03
$9^{th}$ Floor—Baseline—60 min. reduced to 38 min.
$T_2$ Slope: −0.7018
$T_2$ Start Temp: 1248
$T_2$ End Temp: 870
Difference: −378 (−12.6 deg/min)

HTP 9:
Jan. 17, 2007 18:23-18:53
$10^{th}$ Floor—Condition 1 @ 4 hrs.-30 min.
$T_2$ Slope: −0.7413
$T_2$ Start Temp: 1185
$T_2$ End Temp: 940
Difference: −245 (−8.2 deg/min)
35% REDUCTION IN BUILDUP RATE HTP 10:
Jan. 17, 2007 20:09-20:55
$9^{th}$ Floor—Condition 1 @ 6.5 hrs.-60 min. reduced to 51 min.
$T_2$ Slope: −0.2533
$T_2$ Start Temp: 1198
$T_2$ End Temp: 1030
Difference: −168 (−3.3 deg/min)
74% REDUCTION IN BUILDUP RATE HTP 11:
Jan. 19, 2007 19:41-20:01
$10^{th}$ Floor—Condition 2 @ 8 hrs. (Condition 1 @ 54 hrs.)-30 min. reduced to 20 min.
$T_2$ Slope: −1.0159
$T_2$ Start Temp: 1260
$T_2$ End Temp: 1024
Difference: −236 (−11.8 deg/min)
7% REDUCTION IN BUILDUP RATE
Average Buildup Rates:
$10^{th}$ Floor W: −12.8 deg/min
$9^{th}$ Floor NE: −12.6 deg/min
Furnace: −12.7 deg/min

The invention claimed is:

1. A method for measuring ash/slag deposition in an operating utility boiler, comprising:
   i) burning a fuel in the boiler;
   ii) inserting a probe into a zone of the boiler, wherein the probe has multiple thermocouples therein or thereon for measuring temperatures at different locations along the probe;
   iii) cooling the probe while inserted into the boiler independently of the zone;
   iv) measuring the temperatures at the multiple thermocouples at a baseline time;
   v) adding an amount of an agent selected from the group consisting of a slag control agent, an oxygen generating agent, and a combination thereof to burn with the fuel in the boiler;
   vi) measuring the temperatures at the multiple thermocouples at a time later than the baseline time;
   vii) comparing the temperatures at the multiple thermocouples at the baseline time to the temperatures at the multiple thermocouples at the later time to determine a relative level of deposition and/or rate of deposition of ash/slag; and
   viii) removing the probe from the boiler.

2. The method of claim 1, wherein the probe takes the general shape of a rod.

3. The method of claim 1, wherein the probe has two to four thermocouples.

4. The method of claim 1, wherein the probe is positioned substantially perpendicular to a flame within the boiler.

5. The method of claim 1, wherein the fuel burning in the boiler is fuel oil.

6. The method of claim 1, wherein the fuel burning in the boiler is coal.

7. The method of claim 1, wherein the temperatures are measured in real time.

8. The method of claim 1, wherein the agent is added to the fuel prior to burning.

9. The method of claim 1, wherein after removal of the probe the deposition on the probe at the multiple thermocouples is analyzed for composition and/or thickness.

10. The method of claim 1, wherein the fuel burning in the boiler is coal, wherein the probe takes the general shape of a rod, wherein the probe is positioned substantially perpendicular a flame within the boiler, and wherein the temperatures are measured in real time.

11. The method of claim 1, wherein an amount of the slag control agent is added, wherein the slag control agent is selected from the group consisting of magnesium hydroxide, magnesium carbonate, magnesium organometallic compounds, magnesium carboxylate, magnesium salicylate, magnesium naphthenate, magnesium sulfonate, and magnesium carboxylate with magnesium carbonate overlay.

12. The method of claim 1, wherein the oxygen generating agent is selected from the group consisting of calcium nitrate, calcium organometallic compounds, calcium salicylate, calcium sulfonate, overbased calcium carboxylate, iron oxides, iron carboxylates, iron organometallic compounds, iron sulfonates, barium oxide, barium carbonate, barium carboxylate, barium organometallic compounds, and barium sulfonate.

13. A diagnostic tool for boilers comprising:
a metal probe adapted to have a temperature independent of the operational temperature of the boiler while inserted into the boiler to simulate a boiler tube;
wherein the probe has an elongated exterior surface insertable into and removable from a boiler zone to be analyzed;
wherein the external surface of the probe is located to have deposited thereon ash/slag from the boiler zone, when inserted in the zone, during operation and at least partially retains the ash/slag thereon upon removal of the probe from the boiler zone; and
at least one thermocouple connected to the probe and in operative communication with the exterior surface of the probe to measure temperature of the exterior surface of the probe at multiple points in time to determine a slope corresponding to a change in temperature at the exterior surface of the probe, wherein the exterior surface of the probe surrounds an internal volume, and wherein the internal volume is in communication with a cooling medium to keep the probe at a temperature lower than the temperature of the boiler zone.

14. The tool of claim 13, wherein the cooling medium comprises air.

15. A diagnostic tool for boilers comprising:
a metal probe adapted to have a temperature independent of the operational temperature of the boiler while inserted into the boiler to simulate a boiler tube;
wherein the probe has an elongated exterior surface insertable into and removable from a boiler zone to be analyzed;
wherein the external surface of the probe is located to have deposited thereon ash/slag from the boiler zone, when inserted in the zone, during operation and at least partially retains the ash/slag thereon upon removal of the probe from the boiler zone; and
at least one thermocouple connected to the probe and in operative communication with the exterior surface of the probe to measure temperature of the exterior surface of the probe at multiple points in time to determine a slope corresponding to a change in temperature at the exterior surface of the probe;
wherein the tool is in communication with a cooling medium to maintain the exterior surface of the probe at a temperature cooler than adjacent portions of the boiler zone, and wherein the thermocouple measures the temperature at the exterior surface of the probe, and wherein deposition of slag/ash lowers the temperature measured by the thermocouple.

\* \* \* \* \*